United States Patent
Knebel et al.

(10) Patent No.: US 6,541,658 B2
(45) Date of Patent: Apr. 1, 2003

(54) PROCESS FOR SYNTHESIS OF (METH) ACRYLIC ACID ESTERS BY TRANSESTERIFICATION IN THE PRESENCE OF MIXED CATALYSTS CONTAINING ALKALI METAL CYANATE OR THIOCYANATE

(75) Inventors: Joachim Knebel, Alsbach (DE); Ralf Merbach, Buettelborn (DE); Santa Maria Nuccio, Weiterstadt (DE)

(73) Assignee: Roehm GmbH & Co., KG, Darmstadt (DE)

( * ) Notice: Subject to any disclaimer, the term of this patent is extended or adjusted under 35 U.S.C. 154(b) by 0 days.

(21) Appl. No.: 10/042,208

(22) Filed: Jan. 11, 2002

(65) Prior Publication Data

US 2002/0111511 A1 Aug. 15, 2002

(30) Foreign Application Priority Data

Feb. 12, 2001 (DE) .......................................... 101 06 642

(51) Int. Cl.$^7$ ............................................... C07C 67/02

(52) U.S. Cl. ....................................................... 560/217
(58) Field of Search .......................................... 560/217

(56) References Cited

U.S. PATENT DOCUMENTS 5,486,555 A * 1/1996 Hirata et al.

FOREIGN PATENT DOCUMENTS

JP 55-094380 A * 7/1980

* cited by examiner

Primary Examiner—Johann Richter
Assistant Examiner—Paul A. Zucker
(74) Attorney, Agent, or Firm—Oblon, Spivak, McClelland, Maier & Neustadt, P.C.

(57) ABSTRACT

Acrylic or methacrylic acid esters may be efficiently prepared by the transesterification of a $C_1$ to $C_4$ alcohol ester of acrylic or methacrylic acid and a different alcohol in the presence of a mixture of a) an alkali metal cyanate or alkali metal thiocyanate, and b) an alkaline earth metal oxide, an alkaline earth metal hydroxide or an alkali metal halide.

3 Claims, No Drawings

PROCESS FOR SYNTHESIS OF (METH) ACRYLIC ACID ESTERS BY TRANSESTERIFICATION IN THE PRESENCE OF MIXED CATALYSTS CONTAINING ALKALI METAL CYANATE OR THIOCYANATE

BACKGROUND OF THE INVENTION

1. Field of the Invention

The invention relates to a process for synthesis of esters of acrylic and methacrylic acid, especially esters of higher alcohols and substituted alcohols, by transesterifying esters of acrylic and methacrylic acid with alcohols that are readily available on the large industrial scale, in the presence of mixed catalysts containing alkali metal cyanates.

2. Discussion of the Background

Methacrylic acid esters or acrylic acid esters are usually obtained by the reaction of alcohols with simple methacrylic acid esters such as methyl methacrylate or ethyl acrylate. Alkaline catalysts such as lithium and calcium hydroxides are employed for this purpose, while metal catalysts such as titanium alcoholates or even organotin compounds (German Patents 3423441, 3423443, Röhm GmbH) may also be used. Alkaline catalysts have the advantage of being easily separated from the product, since they can be removed without previous separating processes such as filtration. Their price largely depends upon their lithium content, and so inexpensive catalyst components would be desirable.

Alkali metal cyanides are also known as selective transesterification catalysts (HoubenWeyl, Methods of Organic Chemistry, Volume 5, pages 702 to 703, Thieme Verlag, 1985). Their toxicity, however, limits their possible industrial uses. The less toxic alkali metal cyanates are suitable for transesterification catalysis only in special cases, namely when reactive substrates such as glycidol or carbonate esters are used. For example, German Patent 2525026 (Degussa AG) describes the synthesis of glycidyl methacrylate by transesterification of methyl methacrylate with glycidol in the presence of a transesterification catalyst and a polymerization inhibitor. Potassium cyanide, potassium cyanate and potassium thiocyanate are used as the transesterification catalyst.

Japanese Patent 55094380 also describes a process for synthesis of glycidyl methacrylate by transesterification in the presence of potassium cyanate. The yield of glycidyl methacrylate is 83.5%.

European Patent 683163 describes the synthesis of glycidyl (meth)acrylate by transesterification of methyl (meth)acrylates in the presence of a polymerization inhibitor and a catalyst. The catalyst is synthesized in situ from an ammonium salt or phosphonium halide and potassium cyanide, cyanate or thiocyanate. At the end of the reaction, the catalyst must be deactivated by the addition of alkali metal or alkaline earth metal salts of a sulfonic acid or of a heteropolyacid to the reaction mixture.

SUMMARY OF THE INVENTION

Accordingly, it is an object of the present invention to provide a process for preparing esters of acrylic acid or methacrylic acid, comprising transesterifying an acrylic or methacrylic ester of a $C_1$ to $C_4$ alcohol with a different alcohol, in the presence of a mixed-catalyst system comprising a), an alkali metal cyanate or an alkali metal thiocyanate; and b), an alkaline earth metal oxide, an alkaline earth metal hydroxide, or an alkali metal halide. The process of the present invention avoids the disadvantages of the prior art, in that toxic alkali metal cyanides are not used, and there is no need for additional reaction steps or the addition of materials to deactivate the catalyst. Thus, the process of the present invention is simple, and does not require special deactivation steps which tend to reduce the yield of the special esters formed in the transesterification. In regard to the industrial feasibility of the process of the present invention, the catalyst system of the present invention can be easily separated from the crude ester after the completion of the reaction.

DETAILED DESCRIPTION OF THE INVENTION

The present inventors have found that, in the presence of a mixed-catalyst system comprising a mixture of a), an alkali metal cyanate or alkali metal thiocyanate, and b), an alkali metal or alkaline earth metal salt, alcohols may be converted to the corresponding acrylic or methacrylic acid esters with high purity and with few byproducts, by transesterification with acrylic or methacrylic acid esters of a $C_1$ to $C_4$ alcohol.

Examples of suitable alkali metal cyanates are sodium cyanate or potassium cyanate, and examples of suitable alkali metal thiocyanates are sodium thiocyanate or potassium thiocyanate. The alkali metal cyanates or the alkali metal thiocyanates can be used individually or as mixtures.

The alkali metal salt may be, for example, an alkali metal halide such as sodium chloride, potassium chloride, sodium fluoride, potassium fluoride, sodium bromide, potassium bromide, sodium iodide, lithium chloride, lithium bromide or potassium iodide. The alkaline earth metal salt may be, for example, an alkaline earth metal oxide such as magnesium oxide, calcium oxide or barium oxide. The corresponding hydroxides may also be used.

If the catalyst is a mixture of alkali metal cyanate and alkaline earth metal oxide, the weight ratio of alkali metal cyanate to alkaline earth metal oxide may be 10:1 to 1:2, and may include any range or ratio therebetween, including 9:1, 8:1, 7:1, 6:1, 5:1, 4:1, 3:1, 2:1, and 1:1. If the catalyst is a mixture of alkali metal cyanate and alkaline earth metal hydroxide, the weight ratio of alkali metal cyanate to alkaline earth metal hydroxide may be 50:1 to 1:2, and may include any range or ratio therebetween, including 45:1, 40:1, 35:1, 30:1, 25:1, 20:1, 15:1, 10:1, 9:1, 8:1, 7:1, 6:1, 5:1, 4:1, 3:1, 2:1, and 1:1. If the catalyst is a mixture of an alkali metal cyanate and an alkali metal halide, the weight ratio of the alkali metal cyanate to alkali metal halide may be 5:1 to 1:1, and may include any range or ratio therebetween, including 4:1, 7:2, 3:1, 5:2, 2:1, and 3:2.

The amount of catalyst which may be added to the feed mixture of the $C_1$ to $C_4$ alcohol ester of acrylic or methacrylic acid and the different alcohol to be transesterified, ranges from 0.5% to 5% of the feed mixture, and may include all values and subranges therebetween, such as 1%, 1.5%, 2.5%, 3%, 3.5%, 4%, and 4.5%.

The acrylic or methacrylic acid esters of a $C_1$ to $C_4$ alcohol may include methyl acrylate or methacrylate, ethyl acrylate or methacrylate, propyl acrylate or methacrylate, isopropyl acrylate or methacrylate, butyl acrylate or methacrylate, isobutyl acrylate or methacrylate, sec-butyl acrylate or methacrylate, and tert-butyl acrylate or methacrylate.

In order to provide an industrially feasible process, it is advantageous if the catalyst can be easily separated from the crude ester product without additional process steps after completion of the reaction. A particularly desirable separation process is filtration. A further advantage of the catalyst system of the present invention, compared with the known titanium catalysts, is the water tolerance of the catalyst system of the present invention. The titanium catalysts are deactivated immediately by water in the reaction system, whereas the catalyst system of the present invention is not.

Having generally described this invention, a further understanding can be obtained by reference to certain specific examples which are provided herein for purposes of illustration only, and are not intended to be limiting unless otherwise specified.

EXAMPLES

Apparatus

The feed materials, comprising the alcohol to be transesterified and methyl methacrylate (MMA), was introduced into an apparatus comprising a 0.5-liter three-necked flask with mechanical stirrer, air inlet and top-mounted packed column (30 cm long, filled with 6 mm Raschig rings) as well as column head with reflux splitter. Hydroquinone monomethyl ether was used for stabilization against premature polymerization, and further inhibitors were added as necessary.

Transesterification Conditions

The feed materials were first heated to boiling with the introduction of air, and the azeotrope of MMA and water formed thereby from the wet feed materials was distilled off above the column until the head temperature was constant at 100° C., and clear MMA was distilled over. The bottoms (i.e., the components remaining in the flask that were not distilled off) were then allowed to cool to a temperature of about 90° C., and the quantity of MMA removed by distillation was replenished with pure MMA. The catalyst was added, and the contents of the flask were then reheated to boiling. The resulting azeotrope of MMA and methanol formed, distilled over (head temperature: 65 to 99° C.). Toward the end of the reaction, the head temperature approached the boiling point of pure MMA (100° C. at normal pressure). When only pure MMA was still distilling over, the transesterification was complete. The contents of the flask were then allowed to cool, and the residual MMA was removed under vacuum (about 10 mbar). The catalyst precipitate thus formed was separated by filtration. The filtrate was analyzed by gas chromatography.

Example 1

The feed materials were 32.5 g of ethylene glycol and 300 g of MMA, and the catalyst was 6.65 g (2% relative to the feed materials) of potassium cyanate and 1 g of calcium oxide. The mixture was stabilized with 71 ppm of hydroquinone monomethyl ether, 38 ppm of N,N'-diphenyl-phenylenediamine and 9 ppm of 4-hydroxy-2,2,6,6-tetramethylpiperidyl-N-oxyl (relative to the total feed materials). The resulting mixture was reacted as described above, for 5.5 hours. The yield was 100 g, and the composition of the end product, according to GC analysis was 94.3% ethylene glycol dimethacrylate, 0.53% hydroxyethyl methacrylate, and 4.2% addition products.

Example 2

The feed materials were 31 g of ethylene glycol and 300 g of MMA, and the catalyst was 2 g of sodium cyanate and 1.3 g of lithium chloride (together amounting to 1% relative to the feed materials). The mixture was stabilized with 71 ppm of hydroquinone monomethyl ether, 38 ppm of N,N'-diphenyl-p-phenylenediamine and 9 ppm of 4-hydroxy-2,2,6,6-tetramethylpiperidyl-N-oxyl (relative to the feed materials). The resulting mixture was reacted as described above for 4.5 hours, except that the MMA-containing reaction mixture is filtered, but the MMA was not removed. The yield was 210 g (contains 47.5% MMA), and the composition of the end product according to GC analysis (after subtraction of MMA) was 93.3% ethylene glycol dimethacrylate and 6.7% hydroxyethyl methacrylate.

Comparative Example 3

Potassium Cyanate as the Only Catalyst

The feed materials were 31 g of ethylene glycol and 300 g of MMA, and the catalyst was 3.3 g (1% relative to the feed materials) of potassium cyanate. The resulting mixture was stabilized with 71 ppm of hydroquinone monomethyl ether, 38 ppm of N,N'-diphenyl-p-phenylenediamine and 9 ppm of 4-hydroxy-2,2,6,6-tetramethylpiperidyl-N-oxyl (relative to the feed materials). The resulting mixture was reacted as described above for 4 hours, except that the MMA-containing reaction mixture was filtered, but the MMA was not removed. The yield was 313 g (contains 68.3% MMA). The composition of the end product according to GC analysis (after subtraction of MMA) was 62% ethylene glycol dimethacrylate and 33% hydroxyethyl methacrylate. Thus, a catalyst consisting only of potassium cyanate provided incomplete conversion of the feed materials.

Comparative Example 4

Calcium Oxide as the Only Catalyst

The feed materials were 31 g of ethylene glycol and 300 g of MMA, and the catalyst was 3.3 g (1% relative to the feed materials) of calcium oxide. The resulting mixture was stabilized with 71 ppm of hydroquinone monomethyl ether, 38 ppm of N,N'-diphenyl-p-phenylenediamine and 9 ppm of 4-hydroxy-2,2,6,6-tetramethylpiperidyl-N-oxyl (relative to the feed materials). The resulting mixture was reacted as described above for 4 hours, except the MMA-containing reaction mixture was filtered, but MMA was not removed. The yield was 339 g (contains 73.9% MMA). The composition of the end product according to GC analysis (after subtraction of MMA) was 44.7% ethylene glycol dimethacrylate and 50.3% hydroxyethyl methacrylate. Thus, a catalyst consisting of calcium oxide alone provided incomplete conversion of the feed materials.

Comparative Example 5

Synthesis of N-(methacryloyloxyethyl)-2-imidazolidinone Potassium Cyanate as the Only Catalyst Apparatus 1 liter Witt jar, vane stirrer, air-inlet tube, 50-cm NS45 column with 8×8 mm Raschig rings, column head (liquid splitter), reflux condenser and product cooler, receiver, oil-circulation thermostat for heating, temperature measurement in the bottoms and column head, DEST Star 2 controller and contact celsometer (both from the NGW Co.) to control the drawing off of distillate.

Experimental Procedure

The weighed feed materials were heated to boiling in the absence of catalyst with stirring and slowly introduction of air. Any water present was distilled off azeotropically together with MMA. Thereafter, the contents were cooled to about 10° C., the catalyst and the mass of MMA equivalent to the azeotropic distillate were added, and the contents were heated. The resulting MMA/methanol azeotrope was distilled off at a reflux ratio of 5:1 and a head-temperature limit of 70° C., until the temperature no longer fell below the set limit value. The head temperature was then raised stepwise to 100° C. until only MMA was still boiling at the end of alcoholysis.

Refluxing was continued for a further 10 minutes without drawing off distillate, in order to ensure that alcoholysis had actually ended (constant head temperature). The crude ester was then cooled to room temperature and, after the undissolved catalyst had been separated by means of a fluted filter, the clear filtrate was analyzed by gas chromatography.

The feed materials were 260 g of N-(hydroxyethyl)-2-imidazolidinone and 800 g of MMA, and the catalyst was 2.6 g (1% relative to the imidazolidinone) of potassium cyanate. The resulting mixture was stabilized with 0.7 g of hydroquinone monomethyl ether, 0.24 g of phenothiazine and 0.012 g of 4-hydroxy-2,2,6,6-tetramethylpiperidyl-N-oxyl. The mixture was reacted for 8 hours, and the yield was 823 g. The composition was 56% MMA, 9% unreacted N-(hydroxyethyl)-2-imidazolidinone, 32% N-(methacryloyloxyethyl)-2-imidazolidinone, 0.3% N-(methacryloyloxyethyl)-N'-(methacryloyl)-2-imidazolidinone, and 1% N-(methacryloyloxyethyl)-N'-(2-(methoxycarbonyl)propyl)-2-imidazolidinone. Thus, the transesterification was incomplete.

Example 6

Synthesis of N-(methacryloyloxyethyl)-2-imidazolidinone

The same experimental procedure as in Comparative Example 5 was used, except the feed materials were 260 g of N-(hydroxyethyl)-2-imidazolidinone and 800 g of MMA, and the catalyst was 2.54 g of potassium cyanate and 0.065 g of calcium hydroxide (together amounting to 1% relative to the imidazolidinone). The resulting mixture was stabilized with 0.7 g of hydroquinone monomethyl ether, 0.24 g of phenothiazine and 0.012 g of 4-hydroxy-2,2,6,6-tetramethylpiperidyl-N-oxyl. The mixture was reacted for 4.75 hours, and the yield was 820 g. The composition was 52.6% MMA, 1.5% unreacted N-(hydroxyethyl)-2-imidazolidinone, 38.7% N-(methacryloyloxyethyl)-2-imidazolidinone, 1.76% N-(methacryloyloxyethyl)-N'-(methacryloyl)-2-imidazolidinone, and 3.17% N-(methacryloyloxyethyl)-N'-(2-(methoxycarbonyl)propyl)-2-imidazolidinone.

The priority document of the present application, German application 101 06 642.2, filed Feb. 12, 2001, is incorporated herein by reference.

Obviously, numerous modifications and variations on the present invention are possible in light of the above teachings. It is therefore to be understood that within the scope of the appended claims, the invention may be practiced otherwise than as specifically described herein.

What is claimed as new and is intended to be secured by Letters Patent is:

1. A process for preparing esters of acrylic acid or methacrylic acid comprising:

transesterifying an acrylic or methacrylic ester of a $C_1$ to $C_4$ alcohol with a different alcohol, in the presence of a catalyst system comprising a mixture of:
 a) at least one alkali metal cyanate; and
 b) an alkaline earth metal oxide.

2. The process of claim 1, wherein the catalyst system is present in an amount of 0.5 to 5% relative to the total amount of the acrylic or methacrylic ester of a $C_1$ to $C_4$ alcohol, the different alcohol, and the catalyst system.

3. The process of claim 1, wherein the ratio of alkali metal cyanate to alkaline earth metal oxide ranges between 10:1 and 1:2.

* * * * *